United States Patent
Lee et al.

(10) Patent No.: US 9,228,951 B2
(45) Date of Patent: Jan. 5, 2016

(54) SCANNING APPARATUS

(71) Applicants: Kuan-Lin Lee, Hsinchu (TW);
Chen-Sheng Wu, Hsinchu (TW);
Chun-Hsien Kuo, Hsinchu (TW)

(72) Inventors: Kuan-Lin Lee, Hsinchu (TW);
Chen-Sheng Wu, Hsinchu (TW);
Chun-Hsien Kuo, Hsinchu (TW)

(73) Assignee: SMOBIO TECHNOLOGY, INC.,
Hsinchu (TW)

( * ) Notice: Subject to any disclaimer, the term of this patent is extended or adjusted under 35 U.S.C. 154(b) by 615 days.

(21) Appl. No.: 13/629,985

(22) Filed: Sep. 28, 2012

(65) Prior Publication Data

US 2013/0083189 A1    Apr. 4, 2013

(30) Foreign Application Priority Data

Sep. 30, 2011    (TW) .............................. 100135635 A (51) Int. Cl.
*H04N 7/18*    (2006.01)
*G01N 21/64*    (2006.01)

(52) U.S. Cl.
CPC ........ *G01N 21/6456* (2013.01); *G01N 21/6428* (2013.01); *G01N 2021/6439* (2013.01)

(58) Field of Classification Search
None
See application file for complete search history.

(56) References Cited

U.S. PATENT DOCUMENTS

| | | | |
|---|---|---|---|
| 2008/0073541 A1* | 3/2008 | Vija et al. ................. | 250/363.05 |
| 2008/0213926 A1* | 9/2008 | Tajima et al. .................. | 438/16 |
| 2009/0274360 A1* | 11/2009 | Suzuki et al. ................. | 382/133 |
| 2010/0123089 A1* | 5/2010 | Chen ......................... | 250/474.1 |
| 2011/0115897 A1* | 5/2011 | Najmabadi et al. ............. | 348/79 |
| 2012/0078116 A1* | 3/2012 | Yamashita .................... | 600/476 |

\* cited by examiner

*Primary Examiner* — William C Vaughn, Jr.
*Assistant Examiner* — Eileen Adams
(74) *Attorney, Agent, or Firm* — Ming Chow; Sinorica, LLC (57) ABSTRACT

A scanning apparatus for scanning a biological sample labeled with fluorochrome includes a case, a sample table, a light source module, an image capture unit, and a driving unit. The light source module provides excitation light to the biological sample on the sample table, in which the fluorochrome is excited to generate fluorescence by fluorescence resonance energy transfer. The image capture unit catches images of the fluorescence from the biological sample. The driving unit is connected to the image capture unit to move the image capture unit. The present invention further includes a filter unit on the image capture unit to filter the fluorescence into the image capture unit.

19 Claims, 7 Drawing Sheets

SCANNING APPARATUS

The current application claims a foreign priority to the patent application of Taiwan No. 100135635 filed on Sep. 30, 2011.

BACKGROUND OF THE INVENTION

1. Field of the Invention

The present invention relates generally to a scanning apparatus, and more particularly to a scanning for scanning a biological sample labeled with fluorochrome to obtain an image for observation.

2. Description of the Related Art

With advancement in biotechnology, we pay much attention to test the biological sample, such as protein, cell, and deoxyribonucleic acid (DNA). In prior art, the biological sample is tested by fluorescence detection. In fluorescence detection, fluorochrome has an excitation state and an emission state to mark the specified molecules in the biological sample.

In the past, the researcher has to observe the biological sample by himself/herself to identify and analysis the test's result. However, the intensity of fluorescence will gradually reduce that the researcher may miss the fluorescence mark when he/she observe the biological sample in a time after the test. Besides, the test results for the same sample may be different while the setting conditions, such as volume or weight of fluorochrome added in the sample, or environment conditions, such as temperature or humidity, of the tests are inconsistent.

Consequently, the present invention provides a scanning apparatus to overcome the drawbacks of the prior art.

SUMMARY OF THE INVENTION

The primary objective of the present invention is to provide a scanning apparatus, which may scan the biological sample labeled with fluorochrome for observation.

Another objective of the present invention is to provide a scanning apparatus, which may provide lights with short wavelength in different locations for the biological sample labeled with fluorochrome.

According to the objectives of the present invention above, the present invention provides a scanning apparatus for scanning a biological sample labeled with fluorochrome, including a case having a chamber therein; a sample table provided in the chamber of the case to place the biological sample thereon; a light source module provided in the chamber of the case emits excitation light to the biological sample on the sample table. The fluorochrome in the biological sample is excited to generate fluorescence by fluorescence resonance energy transfer. An image capture unit is provided in the chamber of the case to catch images of the fluorescence from the biological sample. A driving unit connects to the image capture unit to move the image capture unit.

The present invention further includes a filter unit on the image capture unit to filter the fluorescence into the image capture unit.

The scanning apparatus provides the light source module to emit the excitation light to the biological sample. The fluorochrome in the biological sample is excited, and then the driving unit moves the image capture unit to catch the images of biological sample. The present invention provides visible light and invisible light to excite the fluorochrome at the same time or separately to obtain a clear signal observed by researchers. The present invention further catches the images before and after test to adjust the brightness, white balance, or contrast of the image of biological sample in accordance with the difference between the images.

BRIEF DESCRIPTION OF THE DRAWINGS

FIG. 6 is a sectional view of a fifth preferred embodiment of the present invention; and.

DETAILED DESCRIPTION OF THE INVENTION

Figure 1:
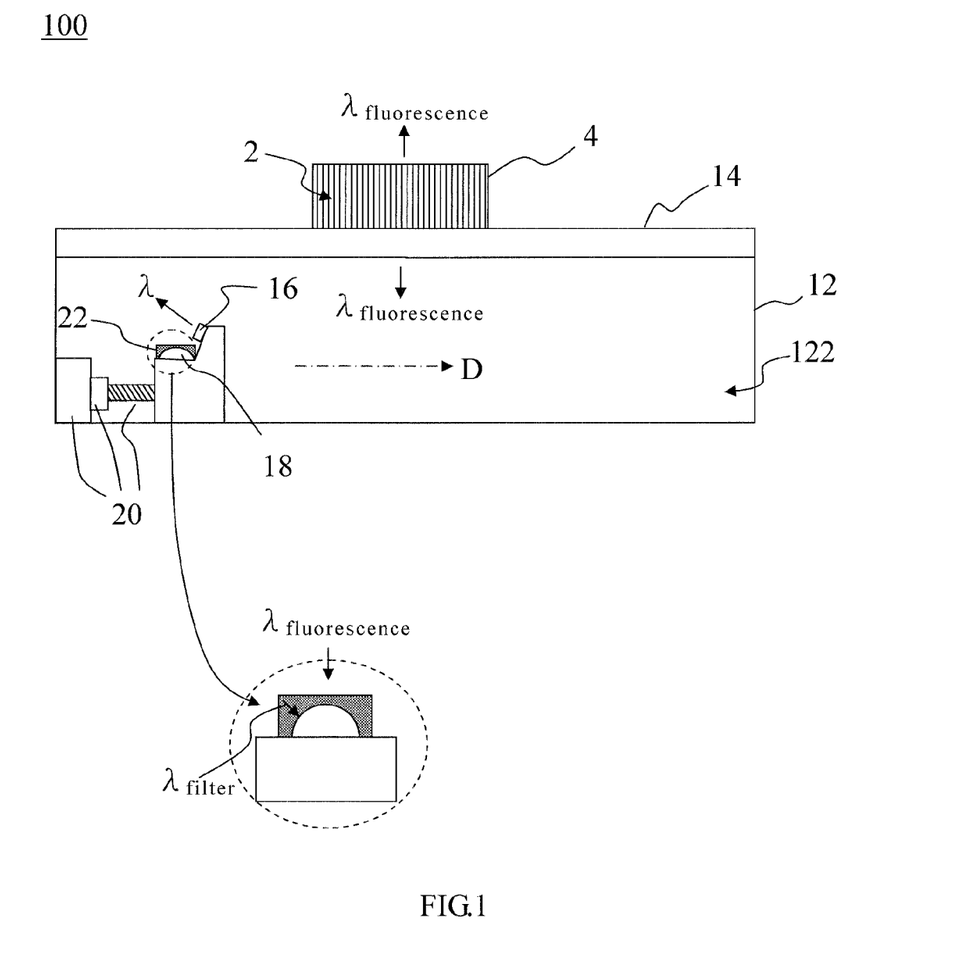
FIG. 1 is a sectional view of a first preferred embodiment of the present invention.

As shown in FIG. 1, a scanning apparatus 100 of the first preferred embodiment of the present invention is to scan a biological sample 4 labeled with fluorochrome 2, so called fluorophore, in a biological test. The biological sample 2 may be gel electrophoresis of deoxyribonucleic acid (DNA), protein, or bio-materials.

The scanning apparatus 100 includes a case 12, a sample table 14, a light source module 16, an image capture unit 18, a driving unit 20, and a filter unit 22. The case 12 forms a cabinet and has a chamber 122 therein. The sample table 14 is provided in the chamber 122 of the case 12 to place the biological sample 4 thereon. The sample table 14 may be transparent or matted.

The light source module 16 is under the sample table 14 to emit excitation light with a short wavelength $\lambda$ to the biological sample 4 in which the fluorochrome 2 is excited by fluorescence resonance energy transfer (FRET) to generate fluorescence with a wavelength $\lambda_{fluorescence}$. The fluorescence may be visible light and invisible light, and the wavelength $\lambda_{fluorescence}$ is in a range between 250 nm and 480 nm, which is between ultraviolet and blue light in the spectrum.

According to the principle of Stokes shift, the wavelength $\lambda_{fluorescence}$ of the fluorescence is greater than the wavelength $\lambda$ of the excitation light. The range of the wavelength $\lambda$ is based on the types of the fluorochrome 2 added in the biological sample 4. The wavelength of the excitation light includes a characteristic wavelength. Thus, we may find a fluorescence emission maximum at a specified emission wavelength (the characteristic wavelength) in the emission spectrum of the fluorochrome 2.

For example, in the range of visible light, the fluorochrome 2 will be excited to generate fluorescence with a wavelength $\lambda_{fluorescence}$ 610 nm while we choose SYPRO RUBY as the fluorochrome 2. The wavelength $\lambda$ of the excitation light from the light source module 16 is between 250 nm and 480 nm, and the characteristic wavelength is 470 nm. In this embodiment, the light source module 16 may be blue LEDs (light emitting diode).

In the range of invisible light, the fluorochrome 2 will be excited to generate fluorescence with a wavelength $\lambda_{fluorescence}$ 610 nm while we choose SYPRO RUBY as the fluorochrome 2. The wavelength $\lambda$ of the excitation light from the light source module 16 is between 280 nm (far ultraviolet) and 380 nm (near ultraviolet), and the characteristic wavelength is 290 nm. In this embodiment, the light source module 16 may be UV lamp or black light tube.

Figure 2:
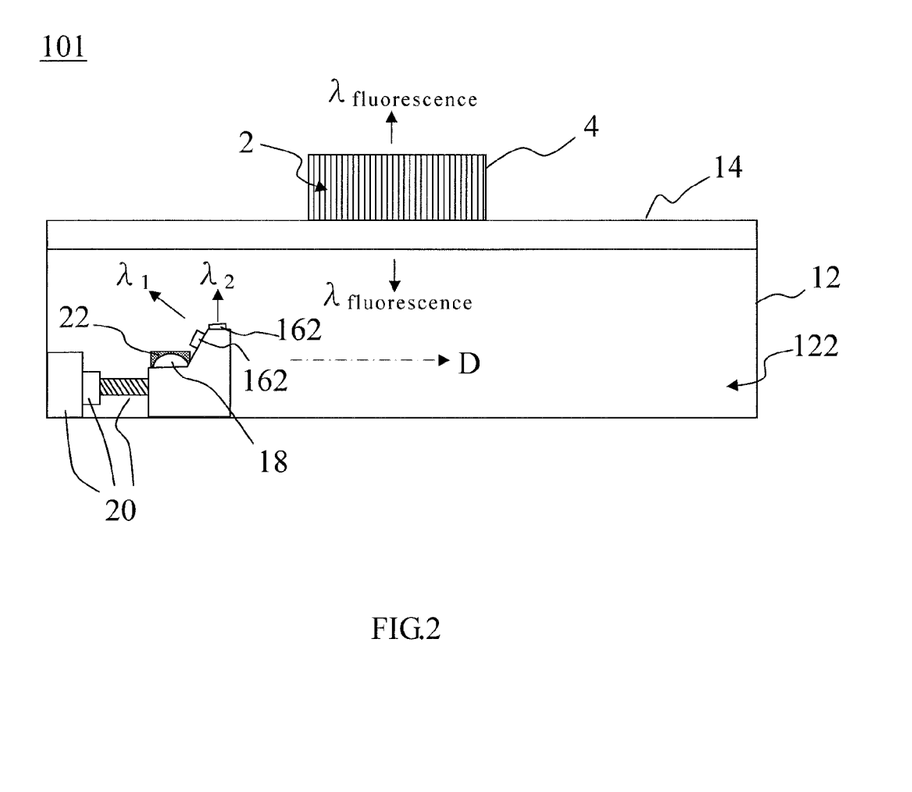
FIG. 2 is a sectional view of a second preferred embodiment of the present invention.

FIG. 2 shows a scanning apparatus 101 as the second preferred embodiment of the present invention, in which the light source module 16 has a plurality of light sources 162 to emit visible light and invisible light. It is noted that different lights have different characteristic wavelengths according to the different fluorochromes 2. Based on this reason, we define a first characteristic wavelength $\lambda_1$ and a second characteristic wavelength $\lambda_2$ here. The specified wavelengths $\lambda$ of the excitation lights from the light source module 16 are selected to excite the fluorochromes 2. Therefore, the excited fluorochromes 2 will generate the fluorescence with the same wavelength $\lambda_{fluorescence}$. For example, the fluorochrome 2 will be excited to generate the fluorescence with a wavelength $\lambda_{fluorescence}$ 610 nm while we choose SYPRO RUBY as the fluorochrome 2, and the light sources 162 emit the excitation lights with the first characteristic wavelength $\lambda_1$ 470 nm and the second characteristic wavelength $\lambda_2$ 290 nm.

Back to FIG. 1, the image capture unit 18 is under the sample table 14 to catch the images of the fluorescence with the wavelength $\lambda_{fluorescence}$.

Figure 3:
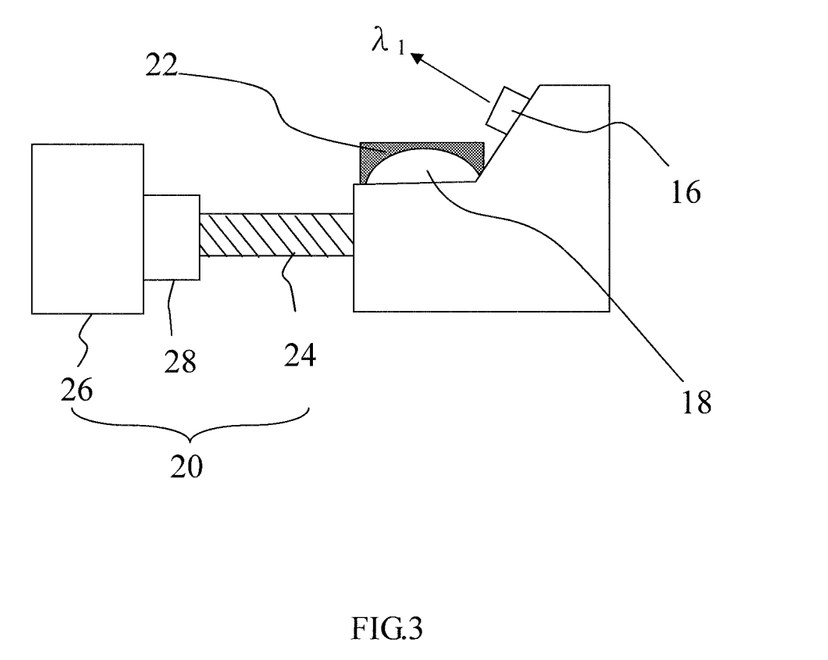
FIG. 3 is a sectional view of the driving device shown in FIG. 1.

The driving unit 20 is connected to the image capture unit 18 to move the image capture unit 18 in a predetermined direction D for scanning all or a part of the biological sample 4. In an embodiment, the driving unit 20 includes a rail 24, a controller 26, and a stepping motor 28. As shown in FIG. 3, the controller 26 controls the stepping motor 28 to drive the image capture unit 18 to move on the rail 24 in a predetermined direction D.

The filter unit 22 is provided on the image capture unit 18 to filter the fluorescence from the biological sample 4 to form fluorescence with a wavelength $\lambda_{filter}$ into the image capture unit 18. The filter unit 22 may be an amber filter.

In the present embodiment, the light source module 16, the image capture unit 18, and the driving unit 20 are under the sample table 14, and the image capture unit 18 neighbors on the light source module 16. Therefore, the light source module 16 and the image capture unit 18 are moved by the driving unit 20 in the same time.

Figure 4:
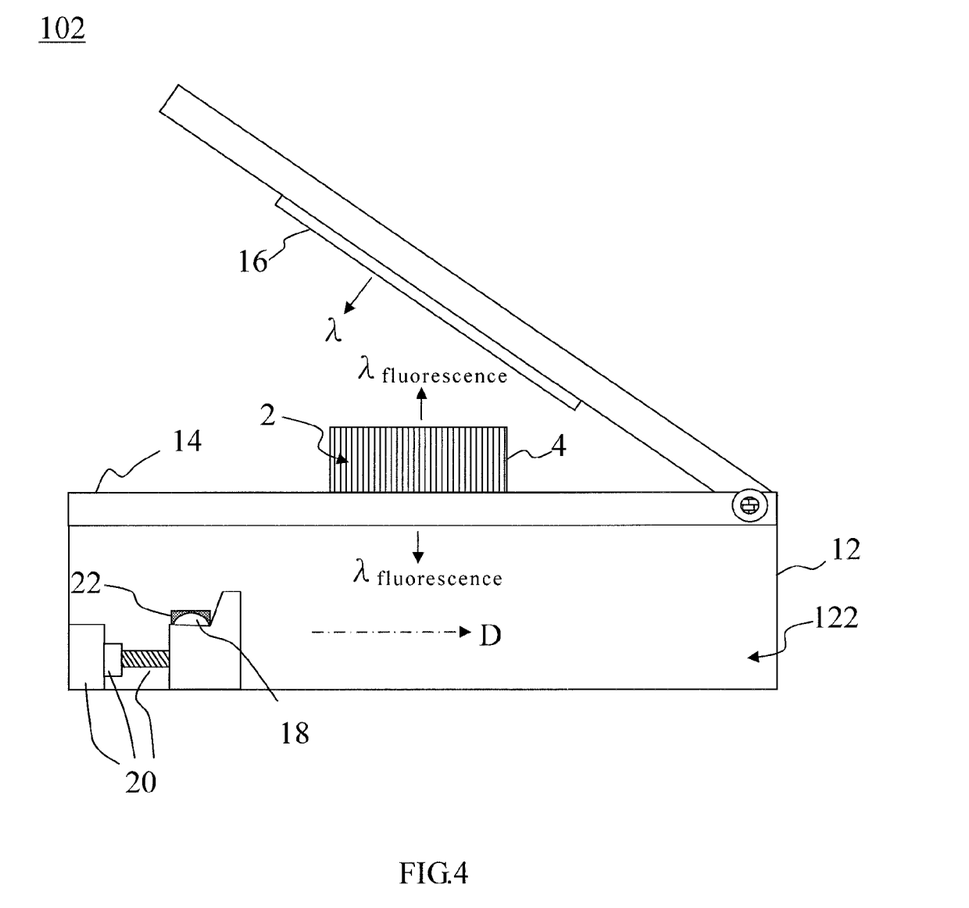
FIG. 4 is a sectional view of a third preferred embodiment of the present invention.

FIG. 4 shows a scanning apparatus 102 of the third preferred embodiment of the present invention including the case 12, the sample table 14, the light source module 16, the image capture module 18, the driving unit 20, and the filter unit 22, the same as above. The difference is that the light source module 16 is above the sample table 14 to emit the excitation light directly to the biological sample 4 on the sample table 14 in a direction diverging from a normal of the sample table 14. The image capture module 18 and the driving unit 20 are under the sample table 14 to catch the image of the fluorescence from the biological sample 4 through the filter unit 22.

It is noted that the light source module 16 may emit the excitation light with single wavelength, or it may include several light sources to emit excitation lights with different wavelengths.

Figure 5:
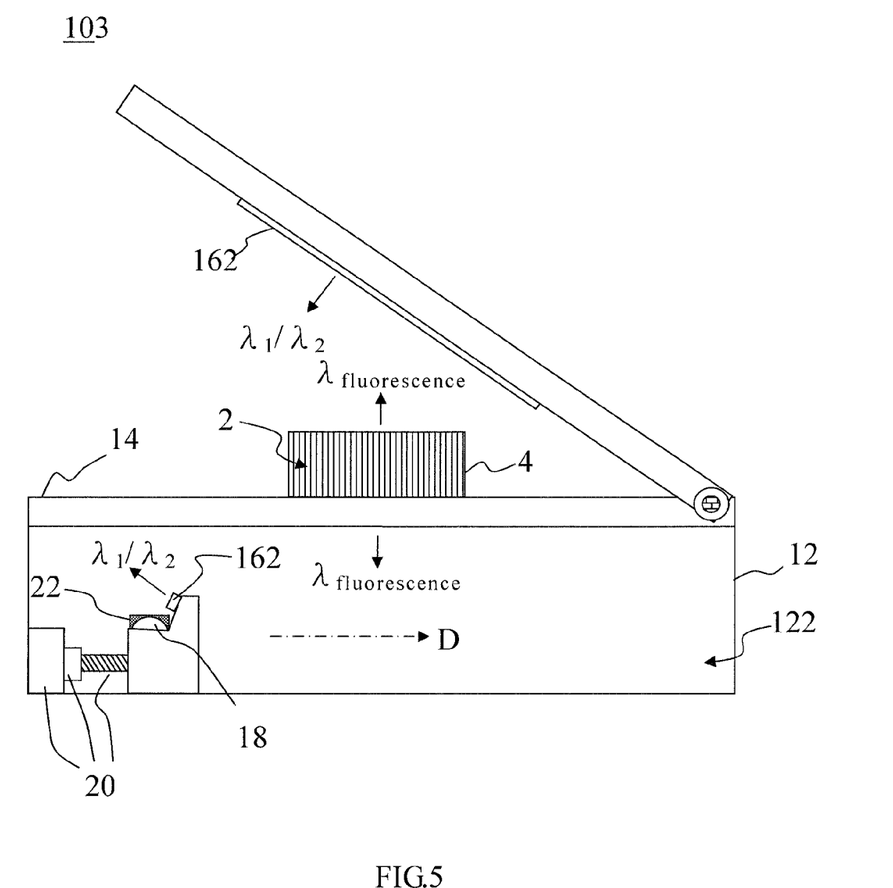
FIG. 5 is a sectional view of a fourth preferred embodiment of the present invention.

FIG. 5 shows a scanning apparatus 103 of the fourth preferred embodiment of the present invention including the case 12, the sample table 14, the light source module, the image capture module 18, the driving unit 20, and the filter unit 22, the same as above. The difference is that the light source module 16 includes a plurality of light sources 162 above and under the sample table 14, respectively. The light sources 162 emit excitation lights with the first characteristic wavelength $\lambda_1$ and the second characteristic wavelength $\lambda_2$. The scanning apparatus 103 of the fourth preferred embodiment may provide stronger excitation light to obtain stronger fluorescence from the biological sample 4. Hence, the image capture module 18 may catch clearer images of the fluorescence.

Figure 6:
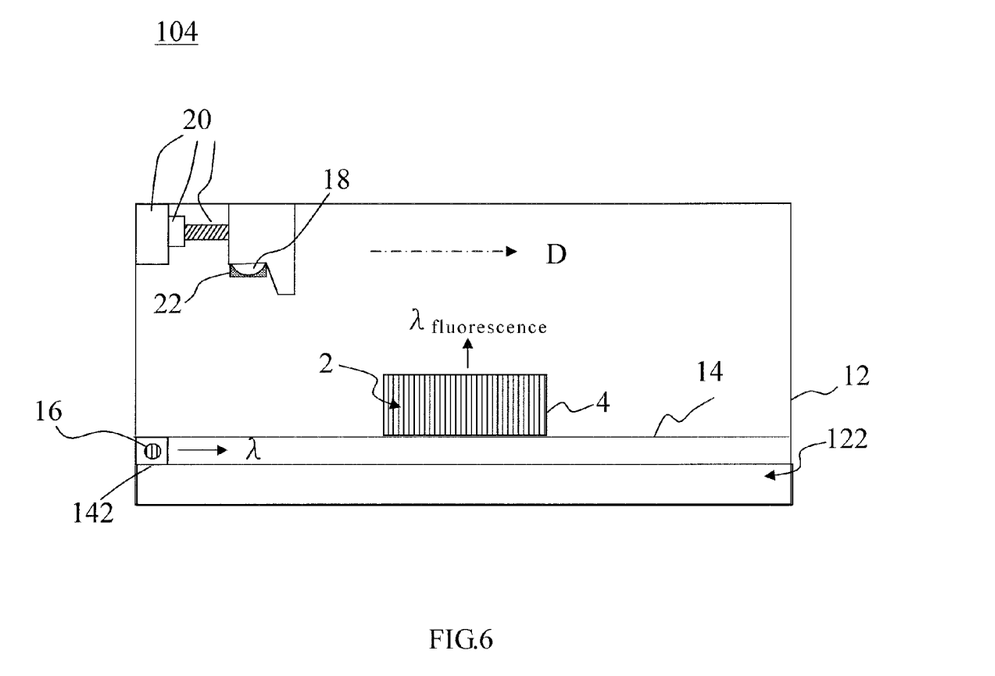

FIG. 6 shows a scanning apparatus 104 of the fifth preferred embodiment of the present invention including the case 12, the sample table 14, the light source module 16, the image capture module 18, the driving unit 20, and the filter unit 22, the same as above. The difference is that the sample table 14 has recesses 142 on an edge to receive the light source module 16 therein, which forms an edge-light backlight. Besides, the image capture module 18, the driving unit 20, and the filter unit 22 are above the sample table 14.

Figure 7:
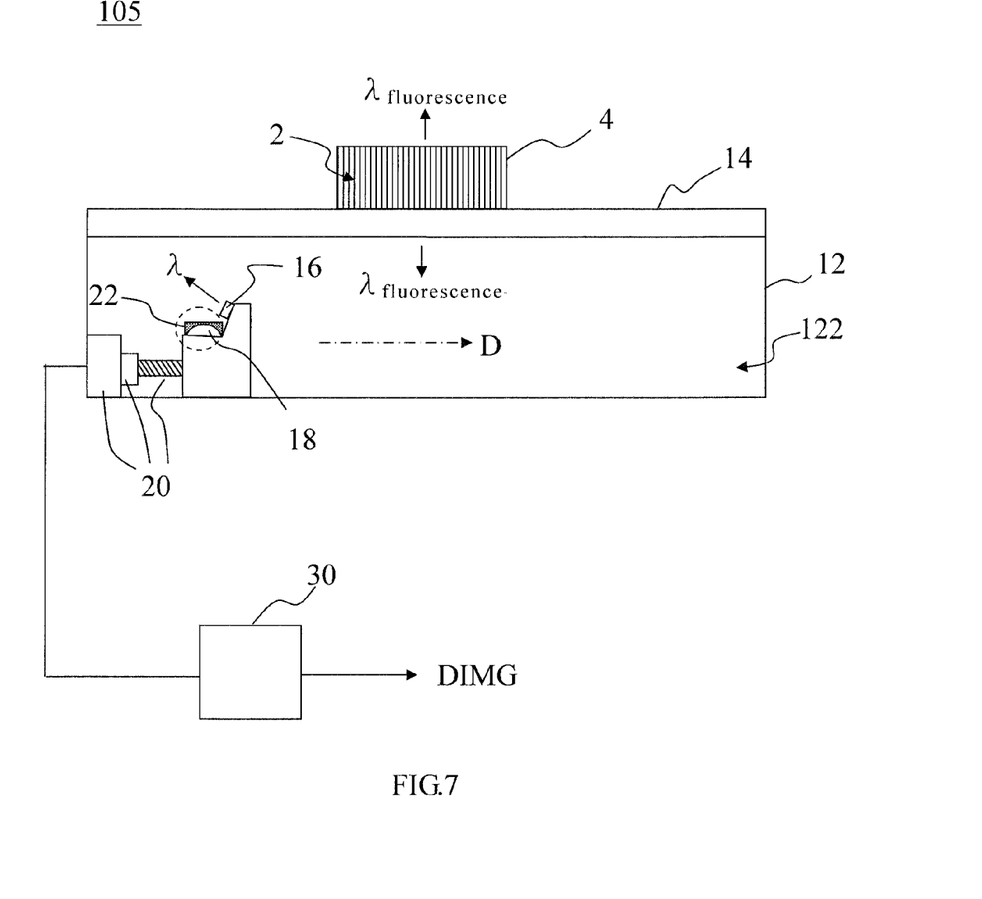
FIG. 7 is a sectional view of a sixth preferred embodiment of the present invention.

FIG. 7 shows a scanning apparatus 105 of the sixth preferred embodiment of the present invention, including the case 12, the sample table 14, the light source module 16, the image capture module 18, the driving unit 20, and the filter unit 22, the same as above. The scanning apparatus 104 of the sixth preferred embodiment further includes a comparison unit 30 connected to the image capture module 18. The image capture unit 24 catches a background image when the biological sample 4 is not put on the sample table 14 yet, and a biological sample image when the biological sample 2 has been put on the sample table 14. The comparison unit 30 compares the biological sample image with the background image and forms a detection image DIMG according to the comparison result. The detection image DIMG may show the difference of brightness, white balance, or contrast.

The scanning apparatus provides the light source module to emit the excitation light to the biological sample, in which the fluorochrome is excited to generate fluorescence. And then the driving unit moves the image capture unit to catch the images of biological sample. The present invention provides visible light and invisible light to excite the fluorochrome at the same time or separately to obtain a clear signal observed by researcher. The present invention further catches the images before and after test to adjust the brightness, white balance, or contrast of the image of biological sample in accordance with the difference between the images.

The description above is a few preferred embodiments of the present invention and the equivalence of the present invention is still in the scope of claim construction of the present invention.

What is claimed is:

1. A scanning apparatus for scanning a biological sample labeled with fluorochrome, comprising:
    a case having a chamber therein;
    a sample table provided in the chamber of the case to place the biological sample thereon;
    a light source module provided in the chamber of the case to provide excitation light to the biological sample on the sample table, in which the fluorochrome is excited to generate fluorescence by fluorescence resonance energy transfer;
    an image capture unit provided in the chamber of the case to catch images of the fluorescence of the biological sample; and
    a driving unit connected to the image capture unit to move the image capture unit in a straight direction parallel to the sample table for catching images of the fluorescence of the biological sample.

2. The scanning apparatus as defined in claim 1, further comprising a filter unit on the image capture unit to filter the fluorescence entering the image capture unit.

3. The scanning apparatus as defined in claim 1, wherein a wavelength of the excitation light is in a range between 250 nm and 480 nm.

4. The scanning apparatus as defined in claim 3, wherein the excitation light has a first characteristic wavelength to excite the fluorochrome to generate the fluorescence.

5. The scanning apparatus as defined in claim 4, wherein a wavelength of the fluorescence from the fluorochrome is 610 nm while the first characteristic wavelength is 470 nm.

6. The scanning apparatus as defined in claim 4, wherein a wavelength of the fluorescence from the fluorochrome is 610 nm while the first characteristic wavelength is 290 nm.

7. The scanning apparatus as defined in claim 1, wherein the excitation light further has a second characteristic wavelength to excite the fluorochrome to generate the fluorescence, and the fluorescence of the fluorochrome excited by the first characteristic wavelength and the second characteristic wavelength has the same wavelength.

8. The scanning apparatus as defined in claim 7, wherein a wavelength of the fluorescence from the fluorochrome is 610 nm while the first characteristic wavelength is 470 nm and the second characteristic wavelength is 290 nm.

9. The scanning apparatus as defined in claim 1, wherein the light source module is under the sample table to emit the excitation light to the biological sample through the sample table.

10. The scanning apparatus as defined in claim 9, wherein the light source module neighbors on the image capture unit, and is move by the driving unit.

11. The scanning apparatus as defined in claim 1, wherein the light source module is above the sample table to emit the excitation light directly to the biological sample.

12. The scanning apparatus as defined in claim 11, wherein the image capture unit is under the sample table to catch the images of the biological sample through the sample table.

13. The scanning apparatus as defined in claim 3, wherein the light source module has a plurality of light sources above and under the sample table, respectively.

14. The scanning apparatus as defined in claim 13, wherein the sample table is transparent or matted.

15. The scanning apparatus as defined in claim 1, wherein the sample table is provided with at least a recess on an edge to receive the light source module therein.

16. The scanning apparatus as defined in claim 1, wherein the driving unit includes a rail to engage the image capture unit, a motor driving the image capture unit to move on the rail, and a controller to control the motor.

17. The scanning apparatus as defined in claim 1, wherein the image capture unit is above the sample table to directly catch the image of the biological sample.

18. The scanning apparatus as defined in claim 1, further comprising a comparison unit connected to the image capture unit to compare the images caught by the image capture unit and to form a detection image according to a result of comparison.

19. The scanning apparatus as defined in claim 2, wherein the filter unit is an amber filter.

\* \* \* \* \*